United States Patent [19]

Bosanquet

[11] Patent Number: 5,650,125
[45] Date of Patent: Jul. 22, 1997

[54] METHOD AND APPARATUS FOR CONDUCTING TESTS

[76] Inventor: Andrew George Bosanquet, Lansdown Croft, Hamilton Road, Bath, United Kingdom

[21] Appl. No.: 411,827
[22] PCT Filed: Oct. 14, 1993
[86] PCT No.: PCT/GB93/02127
 § 371 Date: Apr. 12, 1995
 § 102(e) Date: Apr. 12, 1995
[87] PCT Pub. No.: WO94/09352
 PCT Pub. Date: Apr. 28, 1994

[30] Foreign Application Priority Data

Oct. 14, 1992 [EP] European Pat. Off. .............. 92309364

[51] Int. Cl.$^6$ ...................................................... B01L 3/00
[52] U.S. Cl. ...................... 422/102; 422/72; 422/82.05; 422/99; 422/104; 436/165; 436/177; 436/178; 435/287.1; 435/287.7; 435/288.4; 435/288.7
[58] Field of Search ...................... 422/72, 82.05, 422/82.09, 99, 102, 104; 436/63, 165, 174, 177, 178; 435/287.1, 287.7, 288.4, 288.5, 288.7, 307.1, 809

[56] References Cited

U.S. PATENT DOCUMENTS

| | | | |
|---|---|---|---|
| 3,649,464 | 3/1972 | Freeman | 422/99 X |
| 4,154,795 | 5/1979 | Thorne | 422/102 X |
| 4,319,841 | 3/1982 | Suovaniemi et al. | 422/102 X |
| 4,545,958 | 10/1985 | Dopatka | 422/102 |
| 4,560,535 | 12/1985 | Bouchée | 422/102 |
| 4,682,891 | 7/1987 | de Macario et al. | 422/102 X |
| 4,735,778 | 4/1988 | Maruyama et al. | 422/102 |
| 4,956,150 | 9/1990 | Henry | 422/102 |
| 5,084,246 | 1/1992 | Lyman et al. | 422/101 |
| 5,096,672 | 3/1992 | Tervamäki et al. | 422/102 |
| 5,308,584 | 5/1994 | Vauramo | 422/102 X |

FOREIGN PATENT DOCUMENTS

| | | |
|---|---|---|
| 2204950 | 11/1988 | United Kingdom. |
| 8906162 | 7/1989 | WIPO. |

*Primary Examiner*—Jill Warden
*Assistant Examiner*—Maureen M. Wallenhorst
*Attorney, Agent, or Firm*—Gifford, Krass, Groh, Sprinkle, Patmore, Anderson & Citkowski, P.C.

[57] ABSTRACT

The apparatus includes a receptacle member in the form of at least one row of receptacles for receiving cell samples, each having a closed end and an open end, and a holder adapted to receive the receptacle member in a predetermined orientation and having an abutment for determining the position of a microscope slide relative to the receptacle to allow use of the receptacle member in a centrifuge for sedimentation of the samples through the open ends of the receptacles onto the microscope slide at predetermined positions. The preferred material for the receptacle member is one having a high degree of optical transparency whilst being substantially non-adherent to cells especially tumour cells and several suitable materials are described.

16 Claims, 3 Drawing Sheets

METHOD AND APPARATUS FOR CONDUCTING TESTS

BACKGROUND OF THE INVENTION

The present invention relates to apparatus for use in conducting tests, particularly comparative tests, by a plurality of samples to be tested, and to a method of conducting a test on a plurality of samples.

Without prejudice to the generality of the invention it will be described hereinbelow with specific reference to its application to the performance of a test or assay on cell cultures, especially for the purpose of establishing the effects on the cells of various drugs and concentrations of drugs during an incubation period.

The apparatus of the present invention may be used in the assessment of, for example, the cytotoxic effect of drugs on both normal and tumorous cells. One known apparatus for processing a plurality of samples for subsequent assessment by a technique known as the Differential Staining Cytotoxicity (DiSC) assay is described in WO 89/06162; this apparatus comprises a plurality of separate tubes held in a first rack for incubation and a second rack for centrifugation. This apparatus has proved to be inconvenient since each tube first needs to be placed into the first rack during incubation of the sample in it and then needs to be moved to the second rack or holder for subsequent centrifuging in a cytocentrifuge (for example a Shandon Cytocentrifuge) or similar. There are a number of disadvantages to this known apparatus. A primary disadvantage lies in the fact that the tubes have to be made of a material to which the cells, particularly the tumour cells, are non adherent, or at least have a low adherence so that, upon centrifugation, release of the cells from the tube onto the microscope slide is reliably achieved without there being an unpredictable proportion of the cell population remaining within the tube. Typically, such tubes are made of polypropylene, which is not transparent, but merely translucent.

BRIEF SUMMARY OF THE INVENTION

According to a first aspect of the present invention, there is provided an apparatus for use in forming a plurality of samples on a receiving member, for microscopic examination, comprising a plurality of receptacles each having an open end and a closed end, and a holder for the receptacles allowing assembly to the said receiving member with the interposition of an absorbent member having a plurality of openings and retentions by securing means for holding the receiving member, the absorbent member, the holder and the receptacles together as an assembly with the open ends of the receptacles in contact with the absorbent member and in register with respective openings therein such that, upon centrifugation, supernatant liquid can be absorbed by the absorbent member through the edges of the said openings therein without leakage around the junction between the open end of each receptacle and the respective opening in the absorbent member, characterized in that the receptacles are joined together as a unitary receptacle member comprising at least one row of receptacles, and the holder is adapted to receive the said unitary receptacle member in a predetermined orientation and has means for determining the relative position of the said unitary receptacle member and the said receiving member in forming the said assembly.

For use in the DiSC assay optical transparency is not required whereas non-adherence of tumour cells is essential. The DiSC assay technique involves staining the cells within the tubes with a stain having a differential effect on live and dead tumour cells, and the earlier document WO 89/06162 makes reference to the use of a number of stains, particularly Fast Green and Nigrosin, or a mixture of the two, which are excluded by living cells but stain the dead cells. Upon centrifugation surplus dye is absorbed by an absorbent member together with the remaining supernatant liquid to leave samples of cells on a microscope slide. The above-mentioned earlier document discloses a holder capable of retaining five separate tubes to enable five samples to be deposited on to one microscope slide. The cell samples are then counter-stained with a stain by which live tumour cells are affected, in order to make them visible, and the proportion of dead tumour cells and live tumour cells is then assessed visually by viewing the slide through a microscope and counting the cell population within a given area determined by a microscope grid. For reference purposes an internal standard comprising duck red blood cells is used, these being introduced after incubation and before centrifugation. Counting the cells is laborious and time consuming, especially bearing in mind that, for one patient, up to 600 samples may be required in order to determine the most effective drug or drugs for in vivo treatment.

Preferably, the relative dimensions of the said receptacle member and the said holder are such that the open ends of the receptacles project from a support face of the holder sufficiently between the said open ends of the receptacles and the absorbent member.

In a preferred embodiment of the invention adjacent receptacles are joined together by a web holding them in the said predetermined spaced relationship.

Receptacle members comprising rows of receptacles as such have, of course, been known for a number of purposes in the chemical and medical field where a plurality of comparative tests are required. Various items of commercially available equipment are made to standard dimensions for this purpose. The so-called microtitre format comprises an array of twelve rows of eight receptacles which can be filled, manually or automatically, utilizing multiple outlet micro-pipettes having, for example, eight nozzles allowing eight metered doses of a sample to be introduced simultaneously into all the receptacles of a row. Embodiments of the present invention may conveniently be made to dimensions which allow an array of receptacles, either as a linear array of, for example, eight or a multiple of eight receptacles to be fitted to a microtitre rack support. A single receptacle member may be formed having a plurality of rows and columns, but with overall dimensions such as to fit the microtitre format.

In a preferred embodiment the support face of the said holder is provided with a shoulder against which the said receiving member is engageable to determine its position with respect to the receptacle member. This shoulder or other relative position-determining means preferably locates the receptacle member such that the receptacle at a first end of the row is closer to the adjacent end of the receiving member than the receptacle at the other end of the row to its adjacent end of the receiving member.

Other assay techniques known in the art include determining cell adenosine triphosphate levels (ATP assay), cell metabolism (MTT) and fluorescein diacetate (FDA) assays. All assays require setting up by placing various drugs in different concentrations in contact with respective samples of cells to be assayed, incubating for a period which is typically two or four days, and then determining the effects of the various drugs and concentrations of drugs on the cells by one of the above-mentioned assays. For the DiSC assay, the result is read by staining the dead cells, centrifuging the sample on to a microscope slide, counter-staining the live cells and then counting the cells on the microscope slide. The other assays involve adding different reagents to cause fluorescence or selective absorption or emission of light and reading the results by use of a machine. At present, it has to be decided at the outset which assay to perform since the DiSC assay requires tubes allowing sample release (as disclosed in WO 89/06162) whereas the other assays require optical transmission. It would be more efficient to take a decision after incubation as to which assay to perform, or even to perform the DiSC assay on some samples and perform other assays on the remaining samples. The MTT, ATP and FDA assays are best performed in clear bottomed receptacle, and the DiSC assay requires a non-adherent material (for example polypropylene, which is opaque), but this choice has not been available.

Thus of the assay techniques described above, the ATP, MTT and FDA assays are conducted utilizing a different stain after incubation from that used for the DiSC assay and assessment of the results is achieved mechanically by transmitting light of a given wavelength through the sample and the bottom wall of the receptacle within which the incubation has taken place. The fluorescence (in one case) or depth of absorption (in another case) caused on the cells by the staining, is then determined to obtain an assessment of the cell count by indirect means. The DiSC assay technique however is more accurate, especially where the tumour cell population is a relatively small proportion of the total cell population (say less than 80%) and indeed the other techniques are not reliable at low tumour cell concentrations. The ATP, MTT and FDA assays have the advantage, however, that a large number of samples can be assayed quickly using an automated machine such as a spectrophotometer or a plate reader, but suffers from the disadvantage of spurious readings being given by live cells.

Given that the proportion of normal cells to tumorous cells in the patient's sample is variable when the sample is first taken for assessment, and given that the effects of incubation on this proportion are unpredictable, it is not possible to determine, before incubation, which type of assay is likely to be the most appropriate to use on the samples after incubation. However, the choice of receptacles for incubation has to be made at the outset, and if the receptacles are those suitable for the light-transmission assays (ATP, MTT, FDA) they are not suitable for the DiSC assay since the light-transmissive material is also adherent to cells, especially tumour cells which are particularly "sticky". Should it turn out that the cell population is below the critical threshold, however, the assays involving light measurement are inadequately reliable and the risk of inappropriate treatment based on the results is too great to allow them to be used. Such assays then become wasted. However, not all laboratories are equipped for performing DiSC assays. It would be preferable for the light-measurement assays to be conducted wherever possible, and such assays can be conducted by a large number of hospital laboratories, and for the DiSC assay to be conducted when required. For this purpose, however, the decision must be made before staining on the basis of the tumour cell population proportion, and is only possible if the receptacles in which the cultures have been incubated are suitable to allow reliable release of the cells upon centrifugation. No solution to this problem had been available until the present invention.

One embodiment of the present invention comprises an apparatus by use of which a first step in the process can be conducted and which, upon preliminary investigation after the first step has been conducted, allows the free selection of alternative techniques involving either centrifugation or light-transmission without introducing spurious results or unreliability.

In order to facilitate choice of assay techniques one embodiment of the apparatus of the present invention may be characterized in that the closed ends of the receptacles are defined by respective bottom walls, in that all the bottom walls of the receptacles of a receptacle member lie substantially in a first plane, and in that at least the bottom wall of each receptacle is composed of a material that is at least substantially transparent whereby to allow the sample in the receptacle to be assayed utilizing an optical technique involving the transmission of light through the sample and the bottom wall, or by a technique involving transfer of the sample by centrifugation from the receptacle through the open end thereof onto a receiver.

Each receptacle may have a surrounding flange defining a contact surface for engagement by an absorbent member when performing centrifugation. As described in earlier publication WO/89-06162, centrifugation is performed by introducing a flat absorbent member having a plurality of holes in locations matching the openings in the array of receptacles such that the mouth of a receptacle presses on the perimeter of the cooperating hole such that, upon centrifugation, the supernatant liquid can be absorbed into the absorbent member through the annular surface defining the edge of the hole without leakage of cells or supernatant liquid. In order to avoid excessive compression of the filter member, which must be adequately thick to allow absorption through the edge of each hole, each receptacle preferably has a surrounding flange defining a contact surface for engagement against the absorbent member.

Cell contact during incubation improves the survival rate and is advantageous in avoiding spurious results when assessing the effects of the drugs. In WO 89/06162 the tubes in which incubation takes place have sharply rounded bottom walls for this purpose. However sharp curvature causes optical effects which are disadvantageous for the optical assessment techniques, and embodiments of the present invention therefore provide receptacles having a bottom wall which is curved in cross-section, and rounded at the junction between the bottom wall and the side wall, but in which the curvature of the wall is not so great as to substantially interfere with the transmission of light through the bottom wall.

Having rounded bottom walls, however, means that, especially in the case of linear arrays, these can only be suspended in racks by their flanges unless some other means is provided fox holding them upright. A further embodiment of the present invention is formed as a linear array of receptacles each of which has a rounded bottom wall, with a lower transverse flange projecting therefrom acting as a base to hold the array in an upright orientation with the open ends of the receptacles uppermost. The Base flange can also operate, when the array of receptacles is fitted to the centrifuge holder, to locate the array so that the centre lines of the receptacles are substantially coincident with the radius of the circular path of the array in the centrifuge.

In order to improve the optical properties further, the flanges at the open ends of the receptacles may be formed of or coated with an opaque material thereby limiting the stray light arriving at the sensors when the array is used in a spectrophotometer or plate reader.

Although this bottom wall configuration is preferable, other shapes, including flat walls and v-bottomed walls may be provided if the nature of the intended tests makes this preferable.

The present invention comprehends drug testing apparatus comprising an array of receptacles, each receptacle being open at one end, connected in one or more strips, and covering means covering at least the open end of the receptacles, wherein at least one of the covered receptacle contains one or more drug or the like capable of being used in subsequent testing.

In a preferred embodiment of the above aspect of the present invention, the receptacle member is in standard microtitre format with a single row of eight receptacles or wells, or two adjacent rows of eight receptacles or wells forming a sixteen well strip. Alternatively any other multiple of eight wells adjacent to each other may be provided.

The receptacles may be centrifuged in an "inverted" position in order that the cells may be removed from the receptacles onto the receiving member. In use, liquid is absorbed sideways into the absorbent material as the sample contained therein is deposited by centrifuging onto the receiving member. The receptacles may be of any convenient cross-section but usually will be of circular cross-section (and for convenience will be described hereinafter in relation to such a preferred shape).

In addition, a standard ninety-six well plate may also be formed according to the invention by employing an array of 12 rows of 8 receptacles or "wells". The receiving member onto which samples are deposited by centrifuging may be made sufficiently large to receive all the samples from such an array. A ninety-six well plate may be particularly useful in testing a number of drugs in order to find the cheapest or the most effective. Preferably, the internal diameter of wells in the receptacle member is of the order of 3.5 mm, although other diameters more or less than this are possible. In the past wells have commonly had a diameter of 6 to 7 mm; and although this is possible in the present invention, by reducing the internal diameter to between 3–3.5 mm, it reduces the number of cells required to perform the tests mentioned above by a factor of four. This is of importance in being able to minimize the use of drugs, which are often highly expensive, and also maximize the number of different tests which can be conducted on a given cell sample, which may sometimes be rather small.

The receiving member referred to above is preferably a microscope slide onto which the sample may be sedimented. The absorbent means is preferably a suitably shaped filter paper such as blotting paper. The securing means may take the form of a suitably adapted Shandon holder, which is known in the art.

The receptacles may be made of syndiotactic polypropylene or suspension grade polystyrene in order that, upon centrifuging, any cells in the sample in the tube will not attach to the tube and will be capable of moving onto the receiving member. In addition, these materials are adequately transparent and can therefore be used in MTT, ATP or FDA assays. The receptacles may therefore be used in these assays as well as the DiSC assay. The most satisfactory assay can therefore be selected after incubation.

The receptacles may be sterilized, and drugs in differing amounts and/or of different natures, in a suspending or dissolving medium, are added to some of the wells, frozen, and then the liquid sublimed off in order to provide a pre-prepared set of drugs or the like in solid form for subsequent testing (this process is known as lyophilisation). The drugs are preferably soluble in aqueous media. The provision of such receptacle members in kit form enables simple testing and, for example, when the receptacle members are in the sixteen well form (two rows of eight wells) five different drugs may be provided in duplicate in ten of the wells, two wells may have no drug in them and these may act as negative control wells, and two wells may have a toxic substance in them acting as a positive control well, leaving two wells for any other required use. The covering means may be a wrapper or a cap or strip of caps.

According to a further aspect of the present invention, there is provided a method of conducting a comparative test on a plurality of samples, comprising the steps of introducing a plurality of samples into respective receptacles of apparatus as hereinbefore defined, performing a first operation on the samples in the receptacles, investigating a property of at least one of the samples after the first step has been conducted, and determining, on the basis of the result of that investigation, whether a subsequent step or plurality of steps to be conducted on the samples in situ in the receptacles by a technique involving the transmission of light through the bottom wall of the receptacle, or by extracting the samples by centrifugation through the open ends thereof onto a receiver.

The method defined above may be employed for conducting a comparative test on a plurality of cell samples. In this case the method may be characterized in that the first step in the process is incubation of the cell samples under selected incubation conditions, and the said investigation comprises determining the population of cells of a given type in order to determine the appropriate subsequent steps of the process.

A particularly useful application of the invention is in the assessment of tumour cells, and in this case the cell samples will include tumour cells and the said investigation may comprise an assessment of the percentage of tumour cells present in the cell population at the termination of the incubation stage. The investigation to determine the population of cells may be performed by first extracting the cells through the open end of the plurality of the receptacles by centrifuging onto a receiver such as a microscope slide, and counting the tumour cell population as a percentage of the total cell population.

BRIEF DESCRIPTION OF THE DRAWINGS

Embodiment of the present invention will now be more particularly described, by way of example, with reference to the accompanying drawings, in which.

DETAILED DESCRIPTION OF THE INVENTION

Figure 1:
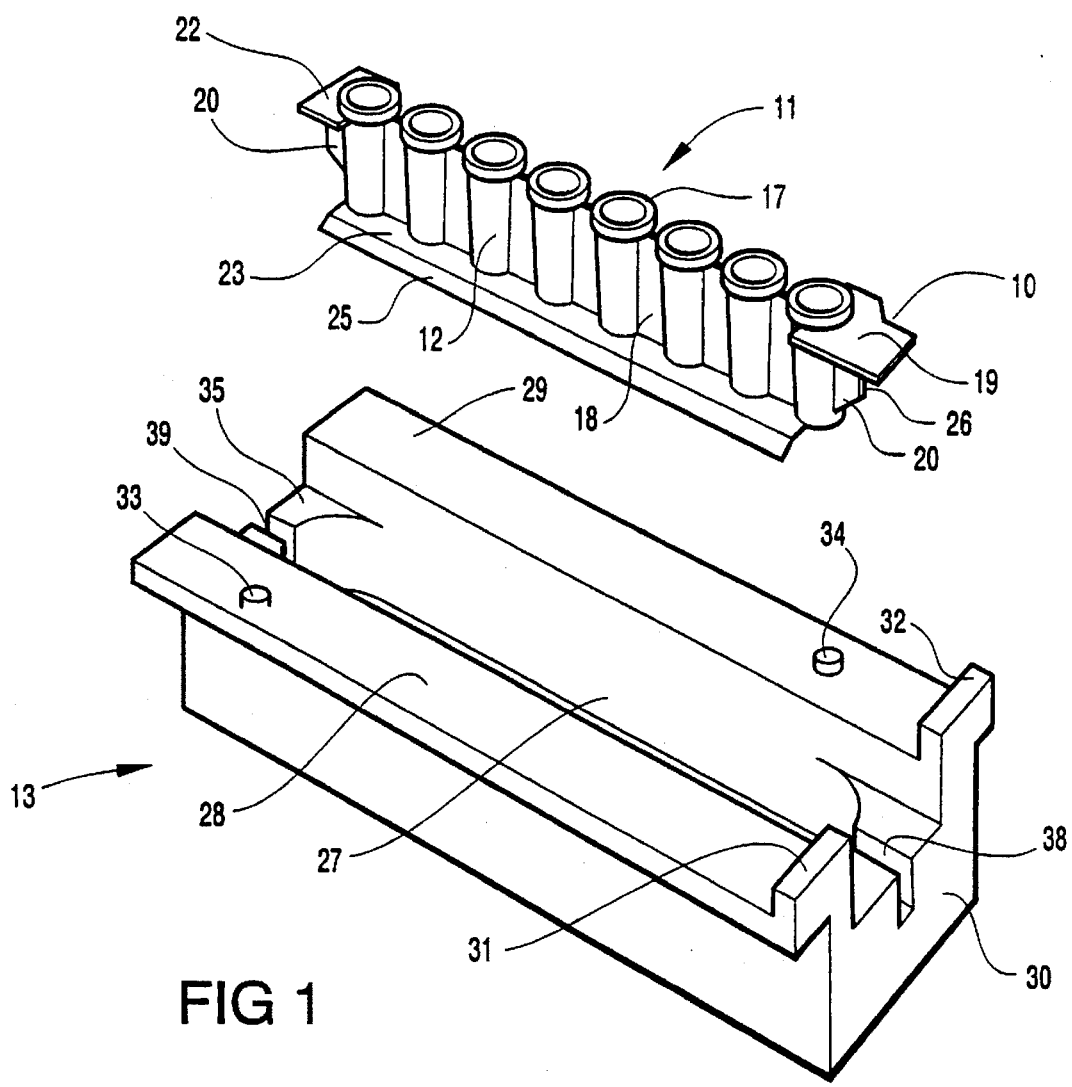
FIG. 1 is a perspective view of an embodiment of the present invention showing the two elements in relative juxtaposition.

Referring first to FIG. 1, the embodiment shown comprises a receptacle member generally indicated 11, having eight upwardly open receptacles or wells each generally indicated 12 in a row, and a receptacle member holder, generally indicated 13 for receiving the receptacle member 11 as will be described in more detail below.

The receptacle member 11 is, in its embodiment, integrally formed of a suitable material such as suspension grade polystyrene or syndiotactic polypropylene, but other materials such as that sold under the trade mark ESCORENE made by Exxon or that sold under the trade reference XB80 12DNA by Nesté may be used. ESCORENE is a very translucent, nearly transparent polypropylene. The particular properties of these materials are that they are adequately clear and transparent without being substantially adherent to cells to allow the preferred method of use described in more detail hereinbelow.

Each receptacle 12 of the receptacle member 11 comprises an open ended generally cylindrical, slightly tapering tubular side wall 14 having an open end 15 and a closed end 16. The open end 15 is surrounded by a flange 17 and each pair of adjacent receptacles 12 is joined by a respective web 18.

The bottom wall 16 is slightly rounded, upwardly concave, and joins the side wall 14 at a rounded corner 118. The diameter of each receptacle 12 is of the order of 3.5 mm at the open end 15 reducing slightly due to the tapering side wall 14. This taper in the side wall is of practical significance only, in permitting the receptacle member to be released from the forming mould more readily. The centre-to-centre spacing or pitch between adjacent receptacles 12 is, in this embodiment, 9 mm to allow use of the apparatus of the invention in cooperation with standard equipment in the so-called microtitre format. A single receptacle member 11, comprising 8 receptacles 12, can be filled from an 8 nozzle micro pipette in a single operation. Such pipettes are known in the art and widely commercially available.

Figure 2:
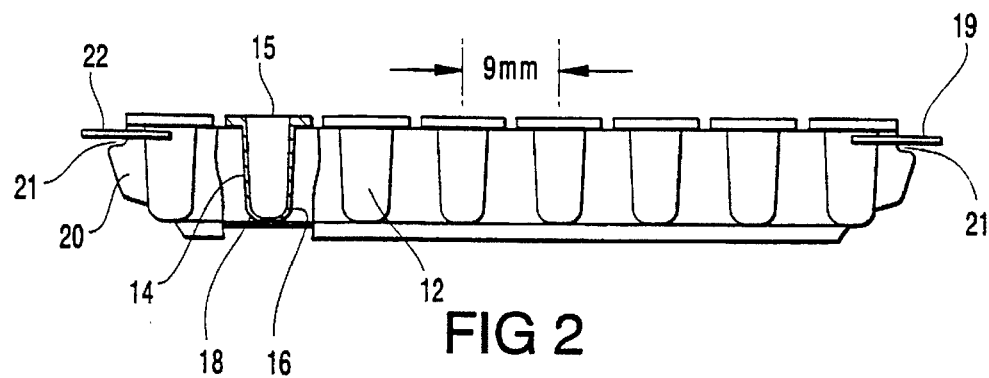
FIG. 2 is a side view on an enlarged scale, of a part of a receptacle member forming one element of the embodiment of FIG. 1.

Projecting from one end of the receptacle member 11, parallel to the plane defined by the flanges 17, but spaced towards the bottom 16 of the receptacle 12 from the open end 15 is an end tab 19 below which is a locating rib 20 having a notch 21 between itself and the tab 19 for snap engagement with a support frame as will be described in more detail below. The tab 19 has a shaped recess 10, as can be seen in FIG. 1, for cooperative engagement with a boss or stud 51 on a microtitre rack 45 (see FIG. 5) to determine the orientation of the receptacle member 11 when positioned on the rack. At the opposite end from the tab 19 there is a shorter tab 22 which has no recess 10, and below which is a rib corresponding in shape to the rib 20 illustrated in FIG. 2.

Projecting from the bottom of the receptacle member 11, laterally of the length thereof, is a transverse base flange 23 having a slightly inclined elongate limb 25 along each of its free edges, the limbs 25 projecting below the bottoms 16 of the receptacles 12 to define two parallel supporting edges allowing the receptacle member 11 to be placed on a horizontal surface and remain stably upright despite the rounded bottoms 16 of the receptacles 12.

The dimensions of each receptacle 12, together with its rounded bottom wall 16, allow a smaller cell sample to be used, the rounded bottom encouraging the incubation process by holding the cell sample in a more close-knit arrangement rather than allowing it to spread over a larger bottom wall as is the case with conventional "wells" having a 6–8 mm diameter and a flat bottom wall.

The holder 13 for the receptacle member 11, as shown in FIG. 1, comprises an elongate body having a central recess 27 and two opposite upper lateral flanges 28, 29 which define an upper face of the body 13. At one end 30 of the body 13 the flanges 28, 29 are provided with respective upstanding projections 31, 32 defining shoulders at the said one end 30, and two upstanding studs 33, 34 on respective flanges 28, 29 serve as locating studs as will be described below. The recess 27 is positioned, within the body 13, such as to be offset from a symmetrical position within the body 13, and is further from the end 30 than from the opposite end 35.

At each end of the recess 27 is a respective channel 36, 37 extending down from the upper face of the flanges 28, 29 by a distance less than the full depth of the recess 27, and each channel 36, 37 has a respective longitudinal slot 38, 39 for receiving the ribs 20 at each end of the receptacle member 11 when this is positioned in the recess 27. As will be appreciated, the longer tab 19 at the first end of the receptacle member 11 is intended to fit the longer channel 36 at the end 30 of the body 13, and the shorter tab 22 is intended to fit the shorter channel 37. If the receptacle member 11 is fitted to the channel 27 in the opposite orientation the tab 19 projects from the end of the body 13 and this will prevent the body 13 being fitted to a standard retainer for a centrifuge as will be described in more detail below. The apparatus of the invention therefore is clearly provided with means for identifying the orientation of the receptacle member with respect to the holder.

Figure 4:
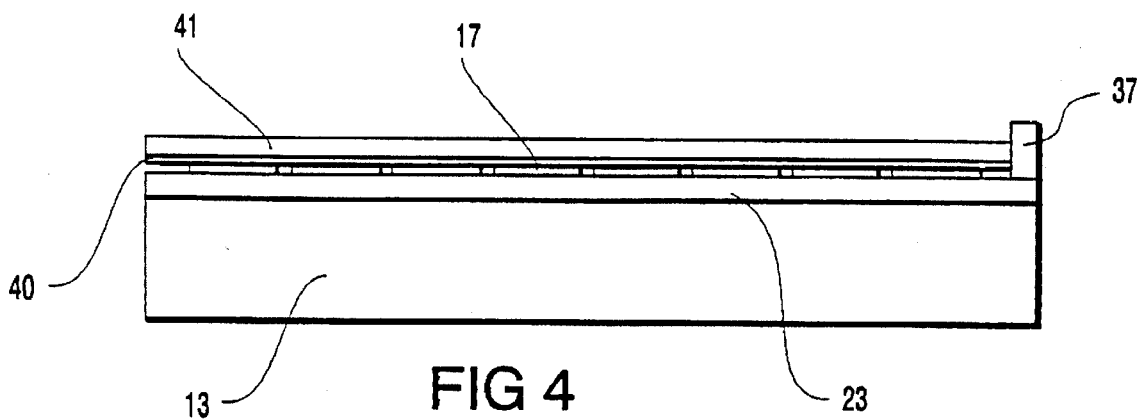
FIG. 4 is a side view of the embodiment of FIG. 1 with the elements shown fitted together.

As can be seen in FIG. 4, when the receptacle member 11 is fitted to the recess 27 the open ends 15 of the receptacles 12 project slightly above the upper faces of the flanges 28, 29, but not so far as the projecting studs 33, 34. The holder body allows the receptacle member 11 to be fitted to a centrifuge by utilizing a standard centrifuge clip such as a Shandon centrifuge retainer, with a microscope slide fitted to the retainer and a suitably shaped filter element positioned between the row of receptacle members and the microscope slide. An example filter member and microscope slide are identified with the reference numerals 40, 41 in FIG. 4. The filter paper and microscope slide, however, do not form part of the apparatus of the invention and are illustrated simply to show the manner in which the apparatus of the invention may be used.

A standard centrifuge retainer can be used to press the microscope slide 41 against the filter paper 40, and this latter against the open ends 15 of the receptacles 12 by engaging under the flanges 28, 29 of the holder 13. The filter paper is thus pressed firmly against the flanges 17 and the microscope slide 41 supported over the whole of its surface area by the filter paper which is compressed between the upper surfaces of the flanges 28, 29 and the flanges 17. The difference in the surface height between the flanges 17 and the flanges 28, 29, is not so great, however, that the pressure exerted by the microscope slide causes significant compression of the paper to cause the filter paper to seal around the openings in the receptacles 12 to prevent absorbtion laterally into the absorbent material, but is sufficiently great to prevent leakage between the absorbent layer and either the microscope slide or the upper surfaces of the flanges 28, 29.

The relative positions of the microscope slide 41 and the row of receptacles 12 is determined by the relative positions of the recess 27 and the shoulders defined by the upstanding ridges 31, 32.

Figure 3:
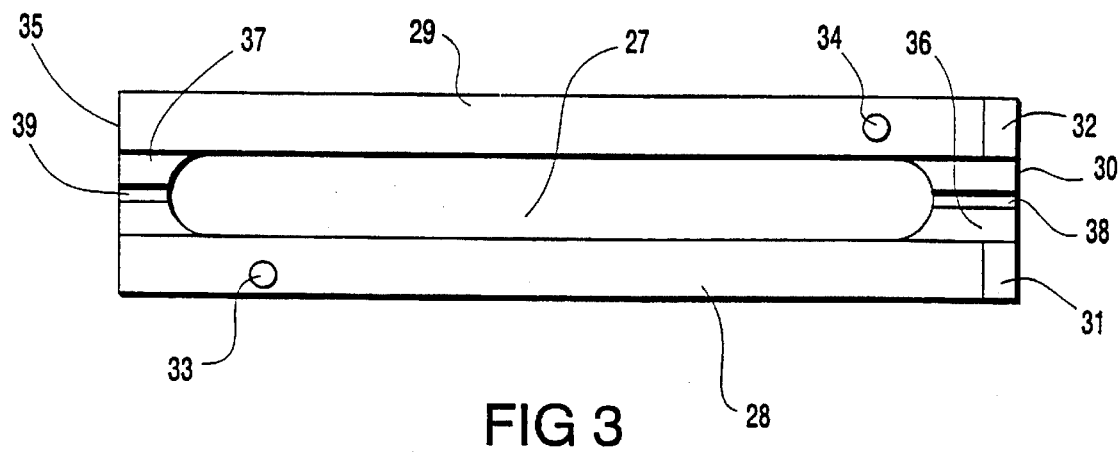
FIG. 3 is a plan view of a receptacle holder forming the second element of the embodiment of FIG. 1.

As will be appreciated by reference to FIG. 3, the distance between the end receptacle 12 and the end of the microscope slide nearest the end 30 of the holder body 13 is slightly greater than the distance between the receptacle at the other end of the row and the opposite end 35 of the holder body 13. This allows a clear visual discrimination between opposite ends of the microscope slide so that it can be positioned in the appropriate orientation. Since the receptacle member 11 can only be positioned within the recess 27 in one orientation the order of the specimens formed on the microscope slide is thus predetermined and cannot be reversed inadvertently.

For identification purposes the microscope slide may be frosted or painted with a suitable markable material along one longitudinal edge over an area such as not to overlap with that to be used for the deposition of samples. By marking along the longitudinal edge of the microscope slide the maximum length available for the positioning of up to eight samples in a single row (or sixteen in two rows of eight) can be utilized.

Figure 5:
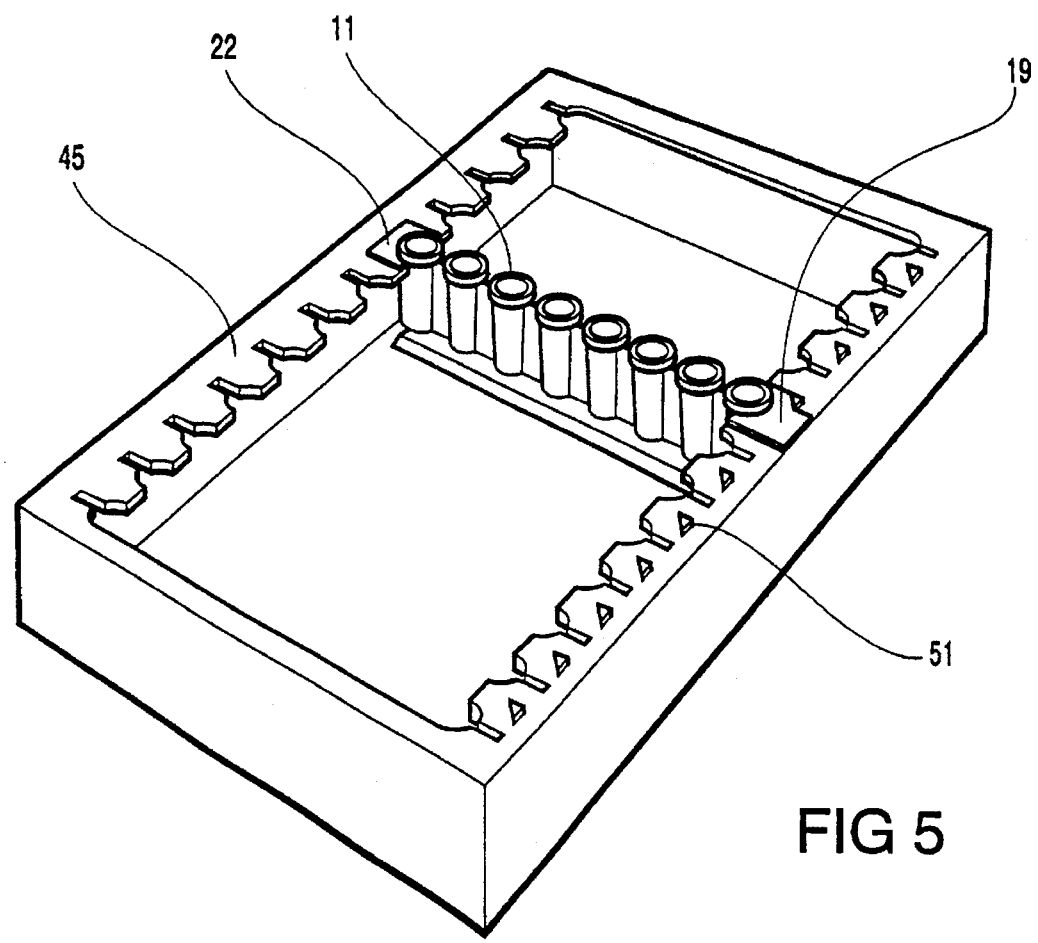
FIG. 5 illustrates in perspective view, a receptacle member forming part of the present invention in place in a microtitre rack.

Finally, FIG. 5 illustrates a conventional microtitre format frame generally indicated 45 showing a receptacle member clipped in position between two opposite limbs. Up to 12 such members may be held on a single rack 45 to provide a 96 well sample array.

In another embodiment of the invention (not illustrated) the receptacle member is formed as a unitary body having ninety-six wells in twelve rows of eight columns, other embodiments may also be formed, for example allowing the formation of arrays having 192 wells, in twenty four rows of eight wells (the rows being spaced 4.5 mm instead of the standard 9 mm) or allowing the formation of arrays having 384 wells, in twenty four rows of sixteen wells (with both the rows, and the wells within the rows, being spaced by 4.5 mm).

I claim:

1. In an apparatus for use in forming a plurality of cell samples on a receiving member for microscopic examination, comprising a plurality of receptacles for samples containing cells to be investigated, each receptacle having an open end and a closed end, a receiving member for said receptacles, an absorbent member defining a plurality of opening arranged for alignment with said open ends of said receptacles for interposition between said open ends of said receptacles and said receiving member, a holder for said receptacles allowing assembly to said receiving member with the interposition of said absorbent member, and securing means for holding said receiving member, said absorbent member, said holder and said receptacles together as an assembly with said open ends of said receptacles in contact with said absorbent member and each open end in register with a respective one of said openings therein whereby, upon centrifugation, supernatant liquid is absorbed by said absorbent member through edges defining said openings therein without leakage around said open end of each receptacle and the respective opening in the absorbent member, wherein the improvement comprises: said receptacles are joined together as a unitary receptacle member comprising at least one row of said receptacles, the internal surface of each said receptacle is at least substantially non-adherent to cell material whereby to allow at least said cells in a said sample to be transferred by centrifugation from each said receptacle through said open end thereof onto said receiving member, said holder receives said unitary receptacle member solely in a single predetermined orientation and has abutment means for abutment by said receiving member whereby to determine the relative position of said unitary receptacle member and said receiving member in an assembly constituted by said holder, said unitary receptacle member received therein, said absorbent member located with said openings in register with said open ends of said receptacles and said receiving member held together by said securing means, and wherein the closed ends of said receptacles are defined by bottom walls lying in a common plane and at least said bottom walls of each receptacle being composed of a material substantially transparent to light to allow the sample in the receptacle to be assayed by an optical technique involving the transmission of light through the sample and the bottom wall.

2. The apparatus of claim 1 wherein said receptacles of said unitary receptacle member are spaced at a substantially constant pitch from each other in said at least one row, and the receptacle at a first end of the at least one row is closer to an adjacent end of said receptacle member than the receptacle at the other end of the at least one row is to an adjacent end of said receptacle member.

3. The apparatus of claim 1, wherein adjacent receptacles in said unitary receptacle member are joined together by a web holding them in a predetermined spaced relationship.

4. The apparatus of claim 1, wherein the center-to-center spacing of adjacent receptacles in said unitary receptacle member is one of substantially 4.5 mm or 9 mm.

5. The apparatus of claim 1, wherein the unitary receptacle member is formed with a lower transverse flange acting as a base to hold the member in an upright orientation with said open ends of the receptacles uppermost.

6. The apparatus of claim 1, wherein the unitary receptacle member comprises a plurality of rows and columns in an array, and at least one row or column is separable from said array as a single unit.

7. The apparatus of claim 1, wherein said holder has a support face, said receptacles have radially projecting flanges at said open ends, said flanges each having an annular end face defining the opening of said open end for contact with said absorbent member in said assembly and a shoulder for abutment with said support face to space each said end face from said support face, and wherein said receptacle member, said holder, said absorbent member and said securing means being so dimensioned that said end faces of said receptacles contact said absorbent member in said assembly without so compressing said absorbent member as to form a seal around said open cads of said receptacles.

8. The apparatus of claim 7 wherein the flanges on said receptacles are formed of or coated with an opaque material.

9. The apparatus of claim 7, wherein said abutment means on said holder comprises a shoulder on said support face against which said receiving member is engageable.

10. The apparatus of claim 7, wherein said absorbent member defines a further opening in addition to and offset from said plurality of openings and said support face on said holder has a locating projection upstanding therefrom for engagement with said further opening to locate said absorbent member in a predetermined position relative to said holder.

11. A kit for use in forming a plurality of cell samples on a receiving member for microscopic examination, comprising:

a plurality of receptacles for receiving media samples containing cell samples to be investigated, each receptacle having an open end and a closed end;

a holder for said plurality of receptacles;

a receiving member for receiving said cell samples from said receptacles;

an absorbent member having edges defining a plurality of openings therein arranged for alignment with said open ends of said receptacles for interposition between said open ends of said receptacles and said receiving member; and securing means for securing said holder with said receptacles therein, said absorbent member and said receiving member together as an assembly with said open ends of said receptacles in contact with said absorbent member and each open end in register with a respective one of said openings therein whereby, upon centrifugation, supernatant liquid is absorbed by said absorbent member through edges defining said openings therein without leakage, around a junction between said open end of each receptacle and the respective opening in said absorbent member, wherein said receptacles are joined together as a unitary receptacle member comprising at least one row of said receptacles, wherein each said receptacle has an internal surface which is at least substantially non-adherent to cell material whereby to allow at least said cell sample to be transferred by centrifugation from said receptacle through said open end thereof onto said receiving member, wherein said holder receives said unitary receptacle member solely in a single predetermined orientation and has abutment means for abutment by said receiving member whereby to determine the relative position of said unitary receptacle member and said receiving member in said assembly and thereby determine the positions at which said cell samples are formed on said receiving member in use and wherein the closed ends of said receptacles are defined by bottom walls lying in a common plane and at least said bottom walls of each receptacle being composed of a material substantially transparent to light to allow the sample in the receptacle to be assayed by an optical technique involving the transmission of light through the sample and the bottom wall.

12. A kit as claimed in claim 11, wherein said holder has a support face, said receptacle member is received in said holder with said open ends of said receptacles adjacent said support face, said support face has at least one locating projection upstanding therefrom and said absorbent member defines a cooperating aperture offset from said plurality of openings therein for engagement by said at least one locating projection, said at least one locating projection and said cooperating aperture being so positioned as to locate said absorbent member with said plurality of openings in register with said open ends of the receptacles in said assembly.

13. A kit as claimed in claim 12, wherein said receiving member comprises a microscopic slide and said holder support face has an upstanding shoulder for abutment by said microscopic slide to locate said microscopic slide in a predetermined position for receiving said cell samples.

14. A kit as claimed in claim 11, wherein some of said receptacles contain a drug for use in testing said cell samples.

15. A kit as claimed in claim 14, wherein some of said receptacles contain a drug for use in testing said cell samples and others of said receptacles contain a toxic substance to serve as positive controls for said testing.

16. A kit as claimed in claim 14, wherein some of said receptacles contain no added substance to serve as negative controls for said testing.

* * * * *